(12) United States Patent
Wastchak et al.

(10) Patent No.: US 6,630,449 B2
(45) Date of Patent: Oct. 7, 2003

(54) METHOD FOR REDUCING THE EFFECT OF NICOTINE ADDICTION AND DEPENDANCY

(76) Inventors: David Wastchak, 1709 Secrtariat, Tempe, AZ (US) 85284; Alcinda Miller, 1113 Stanley Ave., North Las Vegas, NV (US) 89030

( * ) Notice: Subject to any disclaimer, the term of this patent is extended or adjusted under 35 U.S.C. 154(b) by 19 days.

(21) Appl. No.: 09/748,647

(22) Filed: Dec. 21, 2000

(65) Prior Publication Data

US 2002/0078969 A1 Jun. 27, 2002

(51) Int. Cl.⁷ .............................................. A61K 38/35
(52) U.S. Cl. ........................................................ 514/12
(58) Field of Search ........................................... 514/12

(56) References Cited

U.S. PATENT DOCUMENTS

| | | | | |
|---|---|---|---|---|
| 4,621,074 A | | 11/1986 | Bourne | 514/12 |
| 5,480,651 A | * | 1/1996 | Callaway | 424/464 |
| 6,132,754 A | * | 10/2000 | Hudson | 424/423 |

OTHER PUBLICATIONS

Bourne, *Treatment of Cigarette Smoking with Short–term High–dosage Corticotrophin Therapy; Preliminary Communication*, J. Royal Soc. Med., 74, 649–650, (1985).

Targovnik, J., *New Strategies to Achieve Successful Smoking Cessation: Clinical Experience of Five Physicians; Perspectives in Clinical Medicine* , (1990).

McElhaney, J., *Respository CorticotrphinInjections as an adjuct to Smoking Cessation During the Initial nicotine Withdrawal Period; Results from a Family Practice Clinic*; Clin. Ther. 11; 854–861, (1989).

Tarogovnik, J., Nicotine, *Corticotrophin and Smoking Withdrawal Symtoms Literature review and Implications for Successful Control of Nicotine Addiction; Clin. Ther*; 11, 846–853, (1989).

\* cited by examiner

Primary Examiner—Phyllis G. Spivack

(57) ABSTRACT

The nicotine addiction associated with smoking can be reduced by a combination of nutrition augmentation, craving reduction, and therapy. The craving reduction is accomplished by administration of adrenocorticotropin and mild relaxants, for example, GABA precursors.

16 Claims, 1 Drawing Sheet

METHOD FOR REDUCING THE EFFECT OF NICOTINE ADDICTION AND DEPENDANCY

BACKGROUND OF THE INVENTION

1. Field of the Invention

This invention relates to methods to reduce the desire to smoke, in particular this invention relates to methods to quit smoking, and most particularly, this invention relates to methods to reduce the craving for nicotine after quitting smoking.

2. State of the Art

Smoking is a huge health problem in the United States, and around the world. For example, every year cigarettes kill more Americans than AIDS, alcohol, car accidents, fires, illegal drugs, murder and suicide combined. Having said this, it is known that smoking is a notoriously hard habit to quit. That is because the smoker is addicted to nicotine, that is to say, the biochemistry of his or her body has become chemically dependant on nicotine, the primary alkaloid found in tobacco. It has been said that the chemical dependance formed by nicotine use can be harder to end than that caused by heroin or cocaine. Indeed, reliance on this chemical dependancy seems to have been one of the tobacco companies main marketing strategies for selling cigarettes and other forms of tobacco.

Of course stopping smoking is one of the single most beneficial life style changes a smoker can do to improve health and increase longevity. It is known that smoking decreases lung capacity and function and is known to cause emphysema and has been implicated in many forms of cancer. It also is harmful to the gums, many other organs of the body, and, most notably, the skin—it causes deep wrinkling. This is in addition to administering to the smoker a large dose of carbon monoxide and other toxins which have a cumulative detrimental effect on the smokers over all health.

A variety of techniques have been suggested to alleviate the craving for nicotine while the smoker tries to quit. These include nicotine replacement therapy-nicotine administered as in Nicoderm®, Nicotderm CQ® and Nicorette®, via patches, gum, spray, inhaler, and the like—and dosing with mild antidepressants, for example, Zyban®, and other medications, for example, Clonidine®, Nortriptyline®, administered orally or transdermally. These methods may work for some people for some periods of time, but the highest success rates for these therapies seems to be about 25%, and most reliable data suggests that, for most people given these therapeutic drugs as they normally are, the success rate is less than 10%.

Administration of corticotrophins provides one alternative method to reduce the craving for nicotine. Bourne, in U.S. Pat. No. 4,621,074 and Bourne, *Treatment of Cigarette Smoking with Short-term High-dosage Corticotrophin Therapy; Preliminary Communication, J. Royal Soc. Med.*, 74, 649 (1985), and others, including Tarogovnik, J., Nicotine, *Corticotrophin and Smoking Withdrawal Symptoms Literature review and Implications for Successful Control of Nicotine Addiction; Clin. Ther.;* 11, 846 (1989); McElhaney, J., *Repository Corticotrophin Injections as an adjuct to Smoking Cessation During the Initial nicotine Withdrawal Period; Results from a Family Practice Clinic; Clin. Ther.* 11; 851 (1989); and Targovnik, J., *New Strategies to Achieve Successful Smoking Cessation: Clinical Experience of Five Physicians; Perspectives in Clinical Medicine* (1990) have found that corticotrophins given to smokers intramuscularly tends to dramatically reduce the craving for nicotine in the smokers so treated. At this time, the exact mode of operation is not well elucidated, but it seems that corticotrophins competes with nicotine for some nicotine receptor site, probably in the brain. About seventy two hours after the first administration, the effect of corticotrophins starts to wear off, and the patient experiences a resumption of nicotine craving. The cravings do not last forever, in many people, they are usually gone within about ten days, but they do come and go with varying intensities until they finally desist. The treatment Bourne described was one administration of corticotrophins. In actual use, this will reduce the cravings for nicotine for perhaps thirty or so days, but then thirty to sixty percent of the patients in this kind of study tend to start smoking again. Obviously, for those who never lost their craving for nicotine, continuing not to smoke presents huge problems, that may not be easily solved by the smoker. The problems with smoking resumption in those no longer really chemically addicted to nicotine tend to involve social settings where others are smoking, the belief that smoking helps in a weight reduction regime, and pleasant associations with smoking.

It would be advantageous to have a system of smoking cessation and nicotine addiction care that lasted long enough to cause at least eighty percent or more of the smokers who participate in the study to no longer have any craving for nicotine, and for those who no longer have a craving for nicotine to remain off tobacco, that is, for at least eighty percent of the smoker who participate in a program to quit smoking for good.

SUMMARY OF THE INVENTION

This invention provides a method of reducing the nicotine addiction associated with smoking by a combination of nutrition augmentation, craving reduction, and therapy. The craving reduction is accomplished by administration of corticotrophins and mild relaxants, for example, tryptophan and GABA precursors.

A first aspect of this invention is a method of treating a smoker trying to quit smoking for nicotine addiction comprising:

administering to the smoker at least one antioxidation agent starting on day one and continuing daily for at least the next thirty days;

co-administering to the smoker at least one vitamin starting on day one and continuing daily for at least the next thirty days;

co-administering to the smoker at least some GABA precursor starting on day one and continuing daily for at least the next thirty days;

administering to the smoker an injection of at least some adrenal corticotropin hormone after the administration of an antioxidant; and administering to the smoker an injection of at least some adrenal corticotropin hormone between sixty and ninety hours after the first administration.

A second aspect of this invention is a method of treating a smoker trying to quit smoking for nicotine addiction comprising:

administering to the smoker at least one antioxidation agent starting on day one and continuing daily for at least the next thirty days;

co-administering to the smoker at least one vitamin starting on day one and continuing daily for at least the next thirty days;

co-administering to the smoker at least some GABA precursor starting on day one and continuing daily for at least the next thirty days;

having the smoker participate in a smoker aversion therapy session by day two and at least one more interval between three and ten days after the first smoker aversion therapy session;

administering to the smoker an injection of at least some adrenal corticotropin hormone after the administration of an antioxidant; and administering to the smoker an injection of at least some corticotrophin hormone between sixty and ninety hours after the first administration.

BRIEF DESCRIPTION OF THE DRAWING

The FIGURE shows in schematic form one preferred course of treatment to reduce the craving for nicotine.

DETAILED DESCRIPTION OF THE PREFERRED EMBODIMENT

Figure 1:
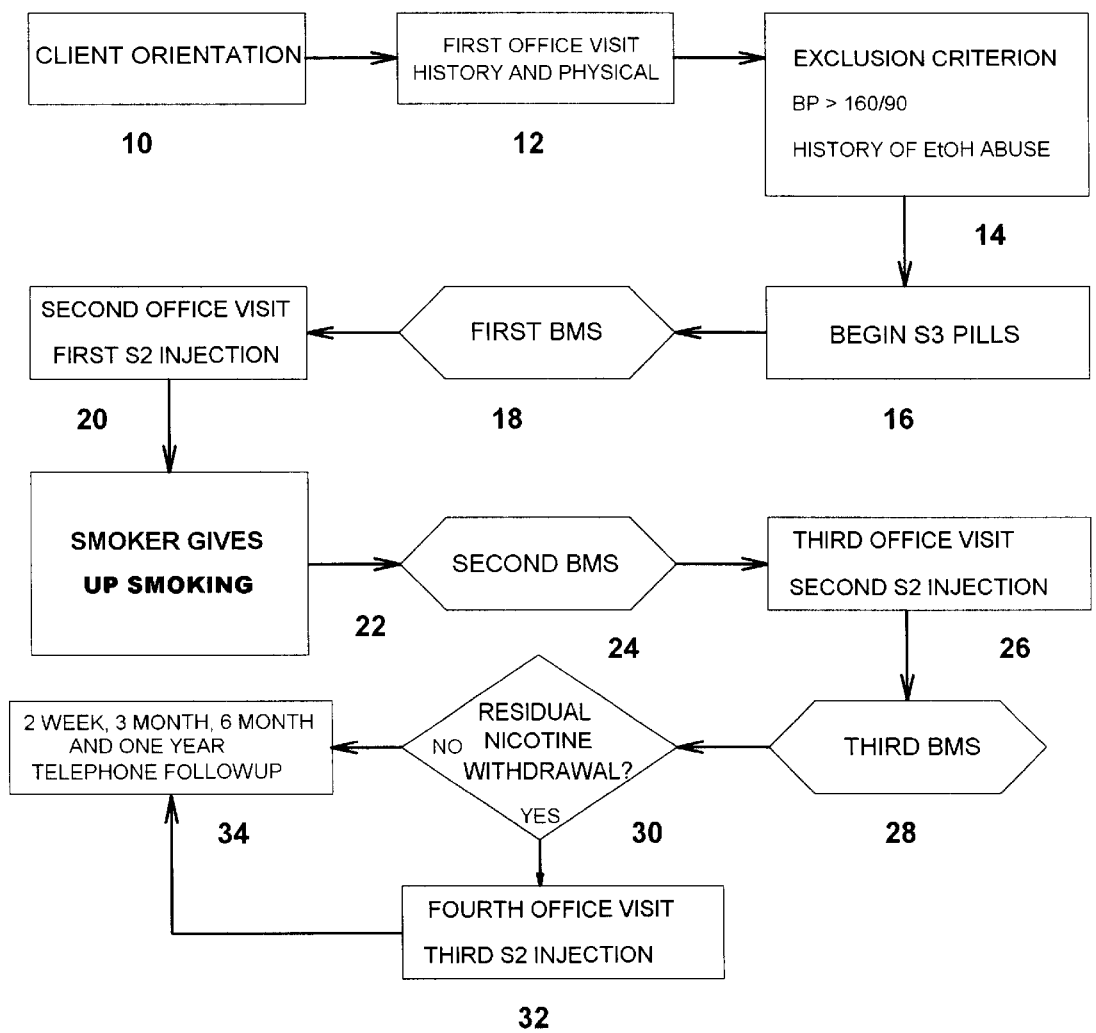

A smoker who wants to quit smoking is first identified. It has been determined that the desire to quit smoking on the part of the smoker is important for the ultimate success of this method. It has been noted that those who do not want to quit smoking, those who are pursuing this course to please a spouse, doctor, parent or the like, will be far less successful in quitting smoking on this or any other treatment. One of the reasons a commitment to quitting smoking is so important in this program is the program outlined herein requires a fairly long term commitment, perhaps thirty days or longer.

After such identification, the smoker who wants to quit smoking begins treatment. Ideally, the treatment comprises a three fold approach; nutrition argumentation, nicotine dependancy relief, and psychological counseling, although in some instances the psychological counseling may be dispensed with.

The nutrition argumentation is important because smoking places numerous toxins within the body and causes extensive oxidative damage by peroxide and other oxidants to lipids and DNA. Natural detoxification of these toxins without augmentation of the needed nutrients can create in the smoker discomfort that may be interpreted by the smoker as nicotine craving, although it is not really. These toxins must be removed by detoxification, usually through the liver, which typically places a high demand on nutrients in the body. Since smoking depletes the body of many vitamins—which one might expect since detoxification is usually a high priority for the body—therefore, fairly high does of vitamins, antioxidants and the like are needed to replenish the smokers body with needed nutrients for the first several months after smoking cessation. It has been observed that providing nutrition will help the smoker stop smoking and stay stopped.

At least one dosage of antioxidant will be administered to the smoker at the beginning of the program—a point in time identified herein as "day one". All days and hours mentioned herein are measured from this arbitrary "day one". The smoker will continue receiving administrations of the antioxidant for at least the next thirty days, more preferably the next sixty days, and most preferably the next ninety days. Preferred antioxidants include vitamin E or α tocopherol, vitamin C or ascorbic acid, β glycine, bioflavonoids, polyphenyls, lipoic acid, green tea, bilberry fruit, gingko, and grape seed extract. The usual mode of administration will be orally, although, depending on the particular antioxidant and the state of health of the patient, other forms of administration including, sub-lingually, transderamally, intramuscularly, internasally, interveniously, can be used. More than one antioxidant can be administered, indeed more than one antioxidant is usually preferred, in the course of this treatment, and administration of more than one antioxidant may be beneficial for the course of treatment since many antioxidants have other beneficial biological effects on the smoker as well.

The smoker will be administered at least one vitamin starting on day one with the administration of the antioxidant and continue administering the vitamin daily for at least the next thirty days, more preferably the next sixty days, and most preferably at least the next ninety days. The vitamin will normally be chosen from the group of vitamins including vitamin A, the B complex of vitamins, especially including B-6 and B-12, Vitamin C and Vitamin D.

The nicotine dependancy relief is attained by administration of Adrenocorticotrophin hormone, hereinafter ACTH or corticotrophin, which is a class of very similar compounds found ubiquitously throughout mammalian species, each species characterized with a slightly different version of the molecule. It is known that its structure is provided by the amino acid chain defined, using the three letter amino acid nomenclature, as [H-Ser-Tyr-Ser-Met-Glu-His-Phe-Arg-Trp-Gly-Lys-Pro-Val-Gly-Lys-Lys-Arg-Arg-Pro-Val-Lys-Val-Try-Pro]-Asp-Gly-Ala-Glu-Asp-Glu-Leu-Ala-Glu-Leu-Ala-Glu-Ala-Phe-Pro-Leu-Glu-Phe-OH. In general only the first 24 amino acid residues (shown in the brackets in the structure above sold under the name Cortrosyn®) form the active part of the molecule and the other residues provide for a species dependent immunomarker for the species. As can be seen, synthetic amino acids can be added to the molecule to increase, decrease or specify potency, and these analogues may be, in some instances substituted for the naturally occurring compound, and such artificial compounds are included in the broadest definition of ACTH and adrenal corticotrophin hormone, which term defines this class of compounds, herein. Administration of corticotrophins is known to stop the craving for nicotine for at lease seventy two hours. The psychological counseling and the like will help the smoker with habits and behaviors the smoker associates with smoking, either consciously or subconsciously.

After the smoker receives his or her first antioxidants, the smoker is administered an injection of at least some adrenal corticotropin hormone. Normally the injection will be of the gel form of corticotrophins. The source of the corticotrophins may be porcine, bovine, equine, or caprine, or any other suitable source. It may include human corticotrophins made using recombinant DNA techniques. The amount will usually be between 40 and 180 units of corticotrophins. The amount of corticotrophins administered will be between about 40 and 320 units of corticotrophins, preferably between about 40 and 225 units, and most preferably between about 80 and 200 units.

It is known that the nicotine relief from the injection of Corticotrophins lasts between about fifty and one hundred hours, more usually between about sixty and ninety hours, and more usually between about seventy and eighty hours. Therefore, between fifty and one hundred hours, more usually between about sixty and ninety hours, and more usually between about seventy and eighty hours from the first administration of corticotrophins the patient will receive a second administration of corticotrophins.

One of the greatest and most annoying symptoms of nicotine withdrawal is the increases most smokers experience in irritability, nervousness, restlessness, mild depression, light headedness, disturbed sleep, anxiety, hunger, and difficulty in concentrating. To combat these symptoms, it has been found that administering mild relaxing agents also helps the process of quitting smoking. Tyrosine, procaine, GABA (also known as γ-aminobutyric acid or 4-aminobutyric acid, a naturally occurring compound that functions as a neurotransmitter) or GABA precursors can be beneficially administered either alone or in conjunction with each other. These will be administered for at least until day thirty, but in no case longer than day ninety. The preferred GABA precursor is procaine. The administration of GABA reduces the anxiety most people feel when they are withdrawing from nicotine.

It has been observed that for the smoker to quit, he or she typically needs some extra psychological support in the form of counseling or therapy, which is sometimes referred to herein as Behavior Modification Session or BMS. The effect of the therapy tends to be more effective if it is administered over several sessions, rather than one intensive session. It has also been determined that sessions having more than one individual trying to quit smoking tend to be more effective to help the smokers quit than one on one sessions with the therapist. The point of the therapy is to cause the patient to disassociate other feeling and behaviors from the bare fact of addiction on the chemical. Presumably, the drug effect of nicotine enhances and promotes behaviors associated with it by the smoker. For example, many people smoke when they speak on the telephone, when they drink, in conjunction with sex, and as a stress coping mechanism. It is important for the smoker to break associations he or she may have with, for example, the telephone, drinking, sex, stress, and coping with stress and smoking. Moreover, certain physical movements, the movement of the cigarette to the mouth, the sucking on the end of the cigarette and the holding of the cigarette, can become very deeply ingrained in the smoker and provide for the smoker pleasant physical sensations. It is important for the patient to be made aware of these problems. One preferred method for encouraging such awareness is a daily diary. Although it is known that groups tend to help smokers quit more effectively than one on one sessions, since each person has individual associations they are trying to break, the details of any persons therapy program will be individualized if the program is to have broad success.

Referring to the FIG. a suitable and preferred process for the treatment of smokers includes nutritional and relaxant supplements, corticotrophin administration, and counseling. On day one, the smoker comes into a clinic for orientation 10. At the time of the first office visit, a medical history is taken and a physical given 12 is taken by the physician, and a determination is made as to whether a given smoker is a satisfactory candidate for treatment 14. High blood pressure, i.e. >160/90, recent intemperate use of alcohol, and other active disease states may suggest to the physician that a given smoker should not be allowed to participate in the program. If the smoker is allowed to participate in the program, the physician will write a prescription of r the needed medications. Then, immediately before the smoker leaves the clinic, a pharmacist fills their prescription for and dispenses to the smoker their supply of nutrition supplements and mild relaxants 16. The next day, day two, the smoker has the first BMS 18. Then on day three the smoker comes back to the clinic and receives the first injection of corticotrophins 20 from the physician. This is the time and place the smoker gives up smoking 22. On day five the smoker participates in a second BMS 24. On day seven, the smoker returns to receive the second injection of corticotrophins 26 from the physician. On day fourteen the smoker, now presumably a former smoker, returns for the last BMS 28. If by the twenty first day the smoker is still experiencing nicotine cravings 30, he or she may come back for a third injection of corticotrophins 32, but if the smoker is free from cravings, the treatment is over, except for followup. It is advantageous to follow the patients progress periodically by telephone for as long as one year to provide support and reassurance to the smoker 34.

This invention can be used to help smokers of all ages, and in particular, can be used to help those 20 years of age and younger to stop smoking.

EXAMPLES

The following examples are provided to illustrate the invention and not in any way to limit the scope of the appended claims.

Example 1

This example shows the typical use of the invention to reduce craving for nicotine in a smoker.

A male smoker, about 250 pounds, who smoked three packs of cigarettes a day, received counseling about the cessation of smoking and the things to avoid, and was dispensed nutritional supplements and given an injection of 160 units of corticotrophin. Although he failed to come back for a second injection of corticotrophin, he ceased smoking permanently despite having a wife who continued to smoke.

Example 2

This example is a comparative example and shows a failed use of the prior art approach to reduce the craving for nicotine and to allow the smoker to stop smoking.

A male smoker, about 170 pounds, who smoked over one pack a day was given an injection of 160 units of corticotrophin. Later, in a comfortable social setting, he resumed smoking to fit in. He unfortunately did not have the real desire to stop smoking, and due primarily to the lack of appropriate counseling he went to places that would encourage resumption of smoking.

This invention has been described by reference to specific embodiments and examples of those embodiments. Those having the usual level of skill in this art have the necessary skills and talents to modify, alter, and vary the embodiments and examples thereof shown herein, without straying from the essential nature of this invention. Therefore, the appended claims are intended to include all such modifications, alterations, and variations.

What is claimed is:

1. A method of treating a smoker for nicotine addiction comprising:
   administering to the smoker at least one antioxidant selected from the group consisting of vitamin E and vitamin C, starting on day one and continuing daily for at least the next thirty days;
   co-administering to the smoker a mild relaxant selected from the group consisting of tyrosine, procaine and GABA precursors, starting on day one and continuing daily for at least the next thirty days;
   administering to the smoker an injection of a pharmaceutically effective amount of a adrenocorticotrophin after receiving said antioxidants; and
   administering to the smoker an injection of adrenocorticotropin between sixty and ninety hours after the first administration.

2. The method of treating a smoker for nicotine addiction of claim 1 further including administering to the smoker a vitamin selected from the group consisting of vitamin A, vitamin B-6, vitamin B-12 and vitamin D.

3. The method of treating a smoker for nicotine addiction of claim 1 wherein the adrenocorticotropin is obtained from animal donors selected from the group consisting of bovine, porcine, equine, and caprine.

4. The method of treating a smoker for nicotine addiction of claim 1 wherein the adrenocorticotropin has only the first 24 residues, the remaining amino acids having been being cleaved off.

5. The method of treating a smoker for nicotine addiction of claim 1 wherein the source of the adrenocorticotrophin is human adrenocorticotrophin obtained from bacterial or fungal species using DNA recombinant techniques.

6. The method of treating a smoker for nicotine addiction of claim 1 wherein the administration is in a gel form.

7. The method of treating a smoker for nicotine addiction of claim 6 wherein the administration of the gel form is selected from the group consisting of subcutaneous injection, intramuscularly injection, and intravenous injection.

8. A method of treating a smoker for nicotine addiction comprising:
   administering to the smoker a pharmaceutically effective amount of an antioxidant selected from the group consisting of vitamin E, and vitamin C, starting on day one and continuing daily for at least the next thirty days:
   co-administering to the smoker a pharmaceutically effective amount of a GABA precursor selected from the group consisting of procaine and procaine salts wherein the counter ion is selected from the group consisting of halides, oxygenated halides, chloride, sulfate, carbonate, and bicarbonate, starting on day one and continuing daily for at least the next thirty days;
   having the smoker participate in a smoker aversion therapy session by day three and day ten after the first smoker aversion therapy session;
   administering to the smoker an injection of a pharmaceutically effective amount of adrenocorticotropin after receiving said antioxidants; and
   administering to the smoker an injection of adrenocorticotropin between sixty and ninety hours after the first administration.

9. The method of treating a smoker for nicotine addiction of claim 8 wherein the method further includes administering to the smoker a vitamin selected from the group consisting of vitamin A, vitamin B-6, vitamin B-12 and vitamin D.

10. The method of treating a smoker for nicotine addiction of claim 8 wherein the adrenocorticotropin is obtained from animal donors selected from the group consisting of bovine, porcine, equine, and caprine.

11. The method of treating a smoker for nicotine addiction of claim 8 wherein the adrenocorticotropin has only the first 24 residues.

12. The method of treating a smoker for nicotine addiction of claim 8 wherein the adrenocorticotropin is of a human source and is obtained from bacterial or fungal species using DNA recombinant techniques.

13. The method of treating a smoker for nicotine addiction of claim 8 wherein the administration of adrenocorticotropin in a gel form.

14. The method of treating a smoker for nicotine addiction of claim 13 wherein the gel is administered via a route selected from the group consisting of subcutaneous injection, intramuscular injection, and intravenous injection.

15. The method of treating a smoker for nicotine addiction of claim 8 wherein the method further includes smoking aversion therapy including a daily diary to be filled in for at least the next sixty days.

16. The method of treating a smoker for nicotine addiction of claim 8 wherein the method further includes smoking aversion therapy including support sessions having at least one other smoker trying to quit smoking.

* * * * *